United States Patent [19]
Commereuc et al.

[11] Patent Number: 5,817,905
[45] Date of Patent: Oct. 6, 1998

[54] PROCESS FOR THE CONVERSION OF ETHYLENE INTO LIGHT ALPHA OLEFINS WITH THE USE OF ADDITIVES BASED ON QUATERNARY AMMONIUM SALTS

[75] Inventors: Dominique Commereuc, Meudon; Yves Glaize, Saint Symphorien D'Ozon; François Hugues, Vernaison; Pierre Panzarella, Maylan; Lucien Saussine, Croissy Sur Seine, all of France

[73] Assignee: Institut Francais du Petrole, France

[21] Appl. No.: 842,504

[22] Filed: Apr. 24, 1997

[30] Foreign Application Priority Data

Apr. 26, 1996 [FR] France ................................ 96 05399

[51] Int. Cl.⁶ .............................. C07C 2/02; C07C 2/08; C07C 2/26
[52] U.S. Cl. .......................... 585/527; 585/520; 585/521; 585/522; 585/523; 585/526
[58] Field of Search ..................................... 585/520, 521, 585/522, 523, 527, 526

[56] References Cited

U.S. PATENT DOCUMENTS

| | | | |
|---|---|---|---|
| 4,855,525 | 8/1989 | Young et al. | 585/523 |
| 5,292,979 | 3/1994 | Chauvin et al. | 585/523 |

FOREIGN PATENT DOCUMENTS 0 578 541   1/1994   European Pat. Off. .

*Primary Examiner*—Elizabeth D. Wood
*Attorney, Agent, or Firm*—Millen, White, Zelano & Branigan, P.C.

[57] ABSTRACT

The invention concerns an improved process for the conversion of ethylene into light alpha olefins wherein the ethylene is brought into contact with a catalyst obtained by mixing a compound of zirconium with an organic compound selected from the class of acetals and ketals, esters, ketones, ethers, amines, nitriles, anhydrides, chlorides of acids, amides, aldehydes, thioethers, sulphides and disulphides, thiophenes, thioureas and phosphines, and with a chloro or bromo compound of aluminium hydrocarbyl, in the presence of an additive formed by at least one quaternary ammonium salt.

25 Claims, No Drawings

PROCESS FOR THE CONVERSION OF ETHYLENE INTO LIGHT ALPHA OLEFINS WITH THE USE OF ADDITIVES BASED ON QUATERNARY AMMONIUM SALTS

FIELD OF THE INVENTION

The present invention concerns an improved process for the production of light alpha olefins by the oligomerisation of ethylene, by virtue of the use of additives based on quaternary ammonium salts.

BACKGROUND OF THE INVENTION

In processes for the oligomerisation of ethylene to form light alpha olefins by means of soluble zirconium-based catalysts, small amounts of solid polymer are formed, which are deposited on and stick to the surface of the reactor and the heat exchanger tubes and which are very harmful to good operation of the process as they reduce the heat transfer effects and necessitate frequent stoppage of the reactor in order for them to be removed.

A known way of reducing the amount of polymer formed involves injecting small amounts of hydrogen (U.S. Pat. No. 4,855,525).

SUMMARY OF THE INVENTION

It has now been found that, if the ethylene oligomerisation reaction is conducted in the presence of additives formed by quaternary ammonium salts, the amount of solid by-product polymer is reduced and in particular the adhesion thereof to the walls of the reactor and the exchangers is considerably reduced.

The invention thus concerns an improved process for the conversion of ethylene into light alpha olefins, wherein, in a reaction enclosure, the ethylene is brought into contact with a solution of a catalyst obtained by mixing a zirconium compound with an organic compound selected from the class of acetals and ketals, esters, ketones, ethers, amines, nitrites, anhydrides, chlorides of acids, amides, aldehydes, thioethers, alkyl sulphides and disulphides, thiophenes, thioureas and phosphines, and with a chloro or bromo compound of aluminium hydrocarbyl, and in the presence of at lest one additive selected from the group formed by quaternary ammonium salts.

Preferably, the ethylene is brought into contact with a solution of a catalyst obtained by mixing at least one zirconium compound with at least one organic compound selected from the class of acetals and ketals and with at least one chloro or bromo compound of aluminium hydrocarbyl, and in the presence of at least one additive selected from the group formed by quaternary ammonium salts.

The elements of the catalyst solution are described for example in European patent EP 578 541, the teachings of which are included herein. More precisely a preferred catalyst is obtained by mixing:

a zirconium compound of the formula $ZrX_xY_yO_z$ wherein X is an atom of chlorine or bromine, Y is a radical selected from the group formed by alkoxy $RO^-$, amido $R_2N^-$ and carboxylates $RCOO^-$, wherein R is a hydrocarbyl radical comprising from 1 to 30 carbon atoms, and x and y may assume integral values of from 0 to 4 and z is equal to 0 or 0.5, the sum x+y+2z being equal to 4, with an organic compound of the formula $(R_1')(R_2')C(OR_1)(OR_2)$ wherein $R_1'$ and $R_2'$ are formed by an atom of hydrogen or a hydrocarbyl radical comprising from 1 to 30 carbon atoms, and $R_1$ and $R_2$ are hydrocarbyl radicals comprising from 1 to 30 carbon atoms, and with an aluminium compound of the formula $AlR''_nX_{3-n}$ wherein R'' is a hydrocarbyl radical comprising from 1 to 6 carbon atoms, X is an atom of chlorine or bromine and n is a number of between 1 and 2.

The components of the catalyst can be brought into contact in any order in a solvent selected from the group formed by aliphatic hydrocarbons such as hexane or heptane, aromatic hydrocarbons such as toluene or ortho-xylene, and the oligomerisation by-products such as higher oligomers. Preferably the zirconium compound is firstly mixed with the acetal or ketal and then the aluminium compound is added to the mixture.

In a particularly advantageous manner the catalyst solution results from the interaction of a mixture of at least one zirconium compound such as for example zirconium tetrachloride and at least one organic compound selected from the class of acetals and cetals, resulting from the condensation of an aldehyde or a ketone with a monohydric alcohol or a polyhydric alcohol such as for example di-(2-ethylhexyloxy)-2,2-propane, with at least one chloro or bromo compound of aluminium hydrocarbyl, for example ethylaluminium sesquichloride.

The molar ratio between the acetal or ketal and the zirconium compound is from 0.1:1 to 5:1, preferably from 0.5:1 to 2:1. The molar ratio between the aluminium compound and the zirconium compound is from 1:1 to 100:1, preferably from 5:1 to 50:1. The concentration of zirconium in the catalytic solution prepared in that way is advantageously between $10^{-4}$ and 0.5 mole per litre and preferably between $2.10^{-3}$ and 0.1 mole per litre. The temperature at which the three components are mixed is normally between $-10$ and $+150°$ C., preferably between 0 and $+80°$ C., for example at a temperature close to ambient temperature (15° to 30° C.). Mixing can be effected in an atmosphere of ethylene or inert gas.

Another catalytic solution as described in U.S. Pat. No. 5,292,979 is also suitable. It results from mixing an alkylzirconate and an ether with an ether/zirconate molar ratio of from 0.5 to 10, with a hydrocarbylaluminium halide.

Mention may also be made of the catalytic solutions described in U.S. Pat. No. 4,855,525, resulting from the interaction of an alkylaluminium with the mixture of a tetrahalide (chloride, bromide) of zirconium and an organic compound selected from the group formed by esters, ketones, ethers, amines, nitrites, anhydrides, acid chlorides, amides and aldehydes.

The catalytic compositions described in patent application EP No. 241 596 can also be used. They are mixtures of zirconium halides with an organic compound of aluminium and a Lewis base selected from the group formed by thioethers, alkyl disulphides, thiophenes, thioureas, sulphides, phosphines, and primary amines.

All the compositions referred to above are set forth by way of non-limiting illustration.

The catalytic solution obtained may be used as it is or else it may be diluted for example by the addition of the products of the oligomerisation reaction.

The quaternary ammonium salts used according to the invention correspond to the general formula $[(R_1R_2R_3R_4)N^+]X^-$ wherein $R_1$, $R_2$, $R_3$ and $R_4$ are identical or different hydrocarbyl radicals, for example alkyl, cycloalkyl, aryl, cycloalkyl or aryl which are substituted by an alkyl group, comprising from 1 to 30 carbon atoms, and X is a monovalent anion, for example a halide or a hydroxide. The following may be mentioned by way of example: tetraethylammonium chloride, tetraethylammonium bromide, trimethyl-cetylammonium chloride, trimethyl-cetylammonium bromide, dimethyl-dilaurylammonium chloride, methyl-trioctylammonium chloride, methyl-tridecylanmonium chloride and benzyl-dimethyl-cetylammonium chloride. Chlorides are the preferred salts. The quaternary ammonium salts may be used as they are (pure) or in the form of a solution in, a hydrocarbon medium selected from the group formed by hydrocarbons and/or light alpha olefins produced by oligomerisation, and/or by the by-products of the reaction such as higher oligomers.

Whether it is a continuous or discontinuous process the quaternary ammonium salts, pure or in solution, may be introduced before proceeding with the ethylene oligomerisation reaction, for example they may be used to effect a treatment for passivation of the walls of the reaction enclosure prior to the reaction being started. The walls of the enclosure are metallic (metals, steels, alloys . . . ) and may have been subjected to protective treatments (polishing, vitrification . . . ) or may have been subjected to anodic protection.

Passivation is effected using any of the known procedures. Advantageously the enclosure is charged with a solution of 20 ppm to 5% by weight of additive in a hydrocarbon medium, contact is maintained preferably with agitation for from 10 minutes to 10 hours, preferably from 30 minutes to 3 hours, at a temperature below the boiling temperature of the solvent, from 20° to 100° C. generally and from 30° to 80° C. preferably. The passivation solution is then generally discharged.

The quaternary ammonium salts, pure or in solution, may also be introduced continuously or discontinuously while the reaction is taking place, for example in the form of a mixture with the solution of the zirconium, preferably in the form of a flow which is independent of the catalyst flows. It may be advantageous to combine a preliminary treatment for passivation of the reaction enclosure, followed by continuous or discontinuous injection while the reaction is taking place.

The amount of quaternary ammonium salts used during the oligomerisation reaction may represent from 1 part per million by weight (ppm) to 5% by weight, advantageously from 1 ppm to 1%, and preferably from 20 ppm to 5000 ppm, with respect to the oligomers produced, whether that amount is introduced during the reaction (continuous process) or into the enclosure prior to the reaction (discontinuous process).

The ethylene oligomerisation reaction can be performed at a temperature of from 20° to 180° C., preferably from 40° to 150° C. and still more preferably from 40° to 130° C. The pressure is from 0.5 to 15 MPa and preferably from 1 to 10 MPa.

In a mode of performing the catalytic oligomerisation reaction discontinuously, the procedure involves introducing into a reactor (reaction enclosure) which is provided with the usual agitation and cooling systems, the additive with the catalyst solution, for example a selected volume of catalytic solution, prepared as described above, and, independently, a selected volume of a solution of quaternary ammonium salt, after which it is pressurised by means of ethylene and the temperature is adjusted to the desired value. The reactor is fed with ethylene at constant pressure until the total volume of liquid produced almost completely fills the reactor. The catalyst is destroyed after reaction, for example by the injection of an amine, and the products of the reaction and the solvents if used are drawn off and separated.

In the case of continuous operation it is advantageously possible to begin each procedure by passivation of the walls of the reactor with a selected volume of a solution of quaternary ammonium salt. After that solution has been drawn off and the reactor advantageously rinsed with a hydrocarbon, the catalytic solution is injected continuously at the same time as and preferably independently of a solution of quaternary ammonium salt and at the same time as the ethylene. The temperature and pressure are kept constant by means of any usual regulating system. The effluent from the reactor is passed, after having been brought into contact with an amine, into a flash column where the effluent treated by the amine is vaporised, either by a rise in temperature or by a drop in pressure or by simultaneous action on temperature and pressure, so as to collect the alpha olefins in the vaporised fraction.

It is desirable to have a maximum degree of vaporisation, for example at least 90% of the volume of the effluent treated with the amine is vaporised, and preferably 95% or more, so as to limit the amount of rejects which will have to be processed in accordance with environmental requirements. However that is not to result in a vaporisation temperature which is prohibitive and indeed harmful to the thermal stability of the olefins. It is preferable to adopt a vaporisation temperature which is lower than or equal to 250° C., preferably 200° C.

The heavy products resulting from the vaporisation operation and containing the deactivated catalyst may be incinerated or treated in any manner which is in accordance with environmental standards.

The vaporised oligomers, according to requirements, are directed to a system of distillation columns which permits separation on the one hand of the unconverted ethylene from the oligomers, which ethylene can be returned to the oligomerisation reactor, and then on the other hand, the oligomers from each other.

The following Examples illustrate the invention without limiting the scope thereof.

EXAMPLE 1

The reaction for the oligomerisation of ethylene is effected in a pilot unit operating in a continuous mode, comprising a reactor of a total volume of 1 litre, operating with a level control giving 0.7 litre of liquid, and fitted with a mechanical agitation arrangement with pneumatic drive. Before the test is started an operation for passivation of the walls of the reactor is effected. To do that, a solution of 0.2 g of tri-(octyl/decyl)-methylammonium chloride (marketed under the name Adogen 464) in 1 kg of ortho-xylene is injected into the reactor, being agitated for 2 hours at a temperature of 90° C. At the end of that period of time the solution of the ammonium salt is drawn off.

The ethylene oligomerisation reaction is then carried out under the following conditions. The procedure involves continuously injecting into the reactor whose temperature is regulated at 90° C. by means of a 20 circulation of oil and in which the pressure is maintained at 7.5 MPa by means of an expansion valve disposed on the outlet line 25.1 g/h of a solution of 2.47 g of sublimated zirconium chloride and 3.18 g of di-(2-ethylhexyloxy)-2,2-propane in 1.13 litre of dried and deaerated ortho-xylene, and 24.3 g/h of a solution of 15.22 g of ethylaluminium sesquichloride in 1.12 litre of dried and deaerated ortho-xylene. 300 g/h of a solution of 0.0079 g of tri-(octyl/decyl-methylammonium in 1.14 litre of ortho-xylene is also continuously injected. Under those conditions the flow rate of ethylene at the intake of the reactor, which is subjected to the level control, is established at 300 g/h. At the discharge from the reactor, 25.5 g/h of a solution of 47.6 g of laurylamine in 1.14 litre of dried and deaerated ortho-xylene is injected on line continuously. The effluent then passes through a flash column operating at a temperature of 150° C. under a pressure of 0.3 MPa. The flashed fraction is passed to a distillation column and the unflashed fraction is collected in a collecting pot. That unflashed fraction which contains the catalyst residues, a part of heavy oligomers which are formed by waxes and a little polymer, represents a flow rate of 20 g/h.

After 80 hours of operation the test is intentionally stopped. The injection of catalyst is stopped first, the consequence of which is a progressive halt in the intake of ethylene, and then after 4 hours, the injection of solvent containing the ammonium salt is stopped and the reactor is allowed to cool. After opening, 20 g of polymer is collected in the form of a granular layer coating all of the internals of the reactor and very easy to detach using the hand. This corresponds to the accumulation of on average 0.25 g/h of polymer in the reactor.

EXAMPLE 2 (Comparative)

The ethylene oligomerisation reaction is effected using the same apparatus and the same mode of operation as in Example 1, under the same conditions in respect of temperature and pressure, and with the same amount of catalyst being injected into the reactor. However, no preliminary treatment for passivation of the reactor is effected and no ammonium salt is continuously injected, that is to say, in addition to the catalyst, 300 g/h of pure ortho-xylene is injected. The flow rate of ethylene at the intake of the reactor is stabilised at 300 g/h. At the discharge from the reactor the effluent is treated as in Example 1. The unflashed fraction which contains the catalyst residues, a part of the heavy oligomers formed by waxes and a little polymer represents a flow rate of 18.5 g/h. The test had to be stopped after 14 hours of operation only, as a result of the mechanical agitation system being locked by the polymer formed. After the reactor is opened, 8 g of polymer is collected, in the form of a compact, hard, strongly adhering mass enveloping a good part of the internal items of equipment. That corresponds to the accumulation of on average 0.57 g/h of polymer in the reactor.

By comparison with Example 1 this Example of the prior art shows that the degree of accumulation of the polymer in the reactor is more substantial and that its adhesion is much greater, which rapidly gives rise to disturbances which are harmful to good operation of the reactor.

EXAMPLE 3

The ethylene oligomerisation reaction is carried out in the same apparatus as in Example 1, the reactor having been passivated beforehand as described in that Example.

The operating conditions are as follows. Continuously injected into the reactor whose temperature is regulated at 90° C. by means of a circulation of oil and in which the pressure is maintained at 7.5 MPa by means of an expansion valve disposed on the discharge line are 18.1 g/h of a solution of 7.74 g of sublimated zirconium chloride and 9.96 g of di-(2-ethylhexyloxy)-2,2-propane in 1.12 litre of dried and deaerated ortho-xylene, and 35.5 g/h of a solution of 31.81 g of ethylaluminium sesquichloride in 1.1 litre of dried and deaerated ortho-xylene. 200 g/h of a solution of 0.067 g of tri-(octyl/decyl)-methylammonium chloride in 1 kg of a 1/1 mixture by volume of heptane and ortho-xylene is also continuously injected. Under those conditions the flow rate of ethylene at the intake of the reactor, which is subjected to the level control, is established at 320 g/h. At the discharge from the reactor, 39.5 g/h of a solution of 84.23 g of laurylamine in 1.04 litre of dried and deaerated ortho-xylene is continuously injected on line. The effluent then passes through a flash column operating at a temperature of 150° C. under a pressure of 0.3 MPa. The flashed fraction is passed to a stablisation column and the unflashed fraction is collected in a collecting pot. That unflashed fraction which contains the catalyst residues, a part of heavy oligomers formed by waxes and a little polymer represents a flow rate of 17.5 g/h. After 68 hours of operation the test is intentionally stopped. The injection of catalyst is stopped first, which has the consequence of progressively stopping the intake of ethylene and then, after 4 hours, the injection of solvent containing the ammonium salt is stopped and the reactor is allowed to cool. After opening about 1 g of polymer is collected in the form of a very fine layer coating the whole of the internals of the reactor and very easy to detach with the finger. That corresponds to the accumulation of on average 0.015 g/h of polymer in the reactor.

We claim:

1. In a process for the conversion of ethylene into light alpha olefins wherein, in a reactor, under effective oligomerization conditions, the ethylene is brought into contact with a solution of a catalyst obtained by mixing a compound of zirconium with an organic compound selected from the class of acetals and ketals, esters, ketones, ethers, amines, nitriles, anhydrides, chlorides of acids, amides, aldehydes, thioethers, alkyl sulphides and disulphides, thiophenes, thioureas, and phosphines, and with a chloro or bromo compound of aluminium hydrocarbyl, the improvement comprising conducting the process in the presence of an amount of at least one quaternary ammonium salt effective to reduce the formation of polymer or adherence of polymer to walls of said reactor.

2. A process according to claim 1 wherein the catalyst solution results from the interaction of at least one chloro or bromo compound of aluminium hydrocarbyl with a mixture of at least one compound of zirconium and at least one organic compound selected from the class of acetals and ketals, resulting from the condensation of an aldehyde or a ketone with a monohydric alcohol or a polyhydric alcohol.

3. A process according to claim 1 wherein the concentration of zirconium in the catalytic solution is between $10^{-4}$ and 0.5 mole per litre.

4. A process according to claim 2 wherein the molar ratio between the aluminium compound and the zirconium compound is between 1:1 and 100:1.

5. A process according to claim 2 wherein the molar ratio between the acetal or the ketal and the zirconium compound is between 0.1:1 and 5:1.

6. A process according to claim 1 wherein the zirconium compound is zirconium tetrachloride.

7. A process according to claim 2 wherein the ketal is di-(2-ethylhexyloxy)-2,2-propane.

8. A process according to claim 1 characterised in that the aluminium compound is ethylaluminium sesquichloride.

9. A process according to claim 1 characterised in that the quaternary ammonium salt is a quaternary ammonium hydroxide or halide.

10. A process according to claim 1 wherein the quaternary ammonium salt is a quaternary ammonium chloride.

11. A process according to claim 1 wherein the quaternary ammonium salt comprises identical or different hydrocarbyl radicals comprising from 1 to 30 carbon atoms.

12. A process according to claim 1 wherein the quaternary ammonium salt is used in the form of a solution in a hydrocarbon medium selected from the group consisting of hydrocarbons, light alpha olefins and oligomers.

13. A process according to claim 1 wherein the quaternary ammonium salt is used in the pure state.

14. A process according to claim 1 wherein, before proceeding with the conversion operation, the quaternary ammonium salt is introduced into the reactor to effect a treatment for passivation of the walls of the enclosure.

15. A process according to claim 1 wherein the quaternary ammonium salt is introduced while the conversion reaction is taking place, the process being continuous.

16. A process according to claim 1, wherein the process being discontinuous, the quaternary ammonium salt additive is introduced into the reactor with the catalyst solution.

17. A process according to claim 1 wherein the quaternary ammonium salt is introduced independently of the catalyst solution.

18. A process according to claim 1 wherein the amount of quaternary ammonium salt used during the conversion reaction is from 1 ppm to 5% by weight with respect to the oligomers produced.

19. A process according to claim 1 wherein the amount of quaternary ammonium salt used during the conversion reaction is from 20 ppm to 5000 ppm with respect to the oligomers produced.

20. A process according to claim 1 wherein the process takes place at a temperature of between 20° and 180° C. under a pressure of from 0.5 to 15 MPa.

21. A process according to claim 6, wherein said organic compound is di-(2-ethylhexyloxy)-2,2-propane) and the chloro or bromo compound of aluminium hydrocarbyl is a chloro compound of aluminium hydrocarbyl.

22. A process according to claim 21, wherein said chloro compound of aluminium hydrocarbyl is ethylaluminium sesquichloride.

23. A process according to claim 21, wherein said quaternary salt is methyl-tri-(octyl)-ammonium chloride, methyl-tri-(decyl)-ammonium chloride, tri-(octyl/decyl)-methylammonium chloride, or mixtures thereof.

24. A process according to claim 22, wherein said quaternary salt is tri-(octyl/decyl)-methylammonium chloride, or mixtures thereof.

25. A process according to claim 1, wherein said at least one quaternary ammonium salt is of the formula $[(R_1, R_2, R_3, R_4)-N^+]X^-$, wherein $R_1, R_2, R_3$, and $R_4$ are identical or different hydrocarbyl radicals having from 1–30 carbon atoms and X is a monovalent anion.

* * * * *